United States Patent [19]

Kurita et al.

[11] 4,018,772

[45] Apr. 19, 1977

[54] PROCESS FOR THE PURIFICATION OF BICYCLOMYCIN

[75] Inventors: Masaru Kurita, Takatsuki; Kazuyoshi Jomon, Kawanishi; Tadaaki Komori, Takatsuki; Isami Nakatani, Ikeda, all of Japan

[73] Assignee: Fujisawa Pharmaceutical Co., Ltd., Osaka, Japan

[22] Filed: Jan. 17, 1975

[21] Appl. No.: 541,929

[30] Foreign Application Priority Data

Jan. 21, 1974 Japan .................................. 49-9481

[52] U.S. Cl. .......................... 260/268 BC; 424/124
[51] Int. Cl.² ............... A61K 35/66; C07D 241/00
[58] Field of Search ............. 424/124; 260/268 BC

[56] References Cited

UNITED STATES PATENTS 3,814,796  6/1974  Argoudelis ..................... 424/124

OTHER PUBLICATIONS

Miyamura et al. – J. of Antibiotics, vol. 26 (1973), pp. 479 and 482–484.
Miyamura et al., J. of Antibiotics, vol. 25 (1972), pp. 610 to 612.

Primary Examiner—Sam Rosen
Attorney, Agent, or Firm—Dayton R. Stemple, Jr.

[57] ABSTRACT

A process for the purification of bicyclomycin by treating a solution thereof with a macroporous nonionic adsorption resin.

6 Claims, No Drawings

PROCESS FOR THE PURIFICATION OF BICYCLOMYCIN

The present invention relates to a new process for purification of bicyclomycin. More particularly, it relates to a new process for purification of bicyclomycin by using a macroporous nonionic adsorption resin.

Bicyclomycin is a known antibiotic isolated from the fermentation broth of a strain of genus Streptomyces, as described in THE JOURNAL OF ANTIBIOTICS, Vol. XXV, No. 10, 569–575, and in German Offenlegungsschrift No. 2150593 in which bicyclomycin is designated as WS-4545 substance.

In this prior literature, there are disclosed processes using certain adsorbents such as activated charcoal, cellulose, silicic acid or diatomaceous earth for the isolation and purification of bicyclomycin from a fermentation broth.

However, these processes have not led to satisfactory practical results in the industrial manufacture of bicyclomycin because they require relatively many steps for the isolation and purification of bicyclomycin, so that the overall recovery of the antibiotic was relatively poor.

Accordingly, it is an object of the present invention to provide a process for obtaining pure bicyclomycin in a relatively good yield.

Another object of the present invention is to provide a new process for purification of bicyclomycin, by which bicyclomycin is obtained more economically than by the prior art processes.

It is a further object of the present invention to provide a new process for purification of bicyclomycin using a macroporous nonionic adsorption resin.

In accordance with the present invention bicyclomycin is purified by adsorbing it from an aqueous solution, wherein it is contained in admixture with impurities, on a macroporous nonionic adsorption resin and then eluted from the resin with a hydrophilic solvent system.

The macroporous nonionic adsorption resins used in accordance with the process of the present invention are the known crosslinked resins having a primary aromatic structure. The preferred resins are styrene polymers crosslinked with divinyl benzene. Examples of such resins are Amberlite XAD-1, XAD-2, XAD-4, XAD-7 and XAD-8 (trademark of Rohm & Haas Co.), Diaion HP 10, HP 20, HP 30, HP 40 and HP 50 (trademark of Mitsubishi Kasei Co., Ltd.), Hitachigel No. 3010 (trademark of Nissei Sangyo Co., Ltd.).

The process for purification of bicyclomycin using the macroporous nonionic adsorption resin in accordance with the present invention is applicable to any aqueous solution containing bicyclomycin admixed with impurities. Examples of such solutions include a filtrate of culture broth per se prepared by cultivating bicyclomycin-producing microorganism in a nutrient medium and a pre-extracted culture solution as well as an aqueous solution containing crude solid material containing bicyclomycin which has been isolated and purified to some degree from a filtrate of the culture broth by means of conventional manners such as an optional treatment of the filtrate with an appropriate solvent for extraction and/or by adsorption on activated charcoal, cellulose, silicic acid or diatomaceous earth.

When using a culture filtrate, it is advantageous to use an optionally pre-extracted culture solution that is then brought into contact with the macroporous nonionic adsorption resin in the usual manner, preferably in a column containing the resin bed. In this pre-operation, it is advantageous to acidify the fermentation broth before filtering it and then to filter it in the usual manner, advantageously in the presence of a filter aid.

The aqueous solution containing bicyclomycin in admixture with impurities is brought into contact with the macroporous nonionic adsorption resin by a conventional manner, e.g., batchwise or columnwise. The adsorbed bicyclomycin can then be eluted with a hydrophilic solvent system from the resin.

For eluting bicyclomycin from the resin, there may be used hydrophilic solvents such as, for example, a lower dialkyl ketone such as acetone, methyl ethyl ketone and methyl isobutyl ketone, or a lower alkanol such as methanol, ethanol, n-propanol, isopropanol, n-butanol, isobutanol, and the amyl alcohols. The ketones contain from 3 to 6 carbon atoms and the lower alkanols contain from 1 to 5 carbon atoms. There may also be used mixtures of the above dialkyl ketone and lower alkanol. Further, mixtures of water or a lower alkyl ester of lower alkanoic acid (e.g., methyl acetate, ethyl acetate and butyl acetate) and the lower alkanol or with the lower dialkyl ketone, lower alkanol or mixtures thereof as above mentioned may also be used.

The aqueous solution containing bicyclomycin in admixture with impurities is brought to pH of from 2 to 8, preferably 4 to 7, prior to being brought into contact with the macroporous nonionic adsorption resin, and the desired pH can be achieved by using any suitable acid, for example, organic acids such as acetic, maleic, succinic and oxalic acids, or preferably a mineral acid such as hydrochloric, phosphoric or preferably sulphuric acid. The spent resin can be readily regenerated by conventional means such as, for example, by washing with an alkaline aqueous or alkaline aqueous-alcoholic solution.

The eluate thus obtained is treated by conventional means such as concentration, lyophilization or crystallization to give crystalline bicyclomycin which frequently is sufficiently pure for use as a medicine.

The following examples are given for the purpose of illustrating the present invention.

EXAMPLE 1

To a culture broth which was prepared by culturing Streptomyces sapporonensis ATCC 21532 at 30° C for 120 hours in 20 liters of a nutrient medium containing 5% of potato starch, 3% of cottonseed meal, 1% of $MgSO_4 \cdot 7H_2O$, 1.09% of $KH_2PO_4$, 0.74% of $Na_2HPO_4 \cdot 12H_2O$, there was added 1% of Radiolite (trademark, a filter aid material sold by Showa Kagaku Kogyo Co., Ltd.) and then the mixture was filtered. One liter of the filtrate (bicyclomycin content: 2.25g) was passed through a column packed with a macroporous nonionic adsorption resin, Amberlite XAD-4 (internal diameter of the column: 5cm, height: 32cm). After the column was washed with water, bicyclomycin was eluted with 1 liter of 50% aqueous acetone to give 800 ml of eluate. The eluate was concentrated to remove acetone and water. To the residue obtained was added 150 ml of a mixture of isopropanol: ethyl acetate (1:2) with stirring and then the solution was filtered. The filtrate was concentrated under reduced pressure to give 1.65g of crystals (purity: almost 100%) of bicyclomycin.

Recovery: 73%.

EXAMPLE 2

1.8g of crystals (purity: almost 100%) of bicyclomycin were obtained by substantially the same procedure as described in Example 1 but using 1.2 liter of 50% aqueous methanol solution as a solvent for elution in place of 50% aqueous acetone used in Example 1.

Recovery: 80%.

EXAMPLE 3

Two liters of the aqueous solution containing 10g of crude crystals (purity: 90%) of bicyclomycin was passed through a column packed with macroporous nonionic adsorption resin, Amberlite XAD-4 (internal diameter of the column: 5cm, height: 32cm). After the column was washed with water, bicyclomycin was eluted with 1 liter of 50% aqueous isopropanol solution to give 600 ml of eluate. The eluate was concentrated under reduced pressure to give 8.6g of crystals (purity: almost 100%) of bicyclomycin.

Recovery: 96%.

EXAMPLE 4

Twenty liters of the filtrate (bicyclomycin content: 2g) of the culture broth which was prepared by culturing Streptomyces griseoflavus var. bicyclomyceticus FERM-P No. 1805 at 30° C for 120 hours in 20 liters of a nutrient medium containing 2% of potato starch, 1% of cottonseed meal, 1% of gluten meal, 1% of soybean meal, 1% of Ebios (trademark) (made by Ebios Yakuhin Co., Ltd.), 2.1% of $KH_2PO_4$ and 1.4% of $Na_2HPO_4 \cdot 12H_2O$ was passed through a column packed with macroporous nonionic adsorption resin, Amberlite XAD-4 (internal diameter of the column: 5cm, height: 32cm). After the column was washed with water, active material was eluted with 50% aqueous acetone. The eluate was concentrated under reduced pressure and then lyophilized to give an amorphous powder. To the powder was added 50 ml of methanol to remove insoluble materials. The methanolic solution was concentrated to give a syrupy residue. The residue was passed through a column of silica gel and then the column was developed with a mixture of chloroform: methanol (10:1). Active fraction was collected, and the solution was concentrated under reduced pressure, and then dried to give white powder. The powder was crystallized from acetone to give 1.5g of crystals (purity: almost 100%) of bicyclomycin.

Recovery: 75%.

EXAMPLE 5

One and a half liters of the filtrate (bicyclomycin content: 3.37g) of the culture broth obtained by substantially the same procedure as described in Example 1 was passed through a column packed with macroporous nonionic adsorption resin, Diaion HP 20 (internal diameter of the column: 5cm, height: 32cm). After the column was washed with 500 ml of water, bicyclomycin was eluted with 600 ml of 50% aqueous acetone. Active fraction was collected, and then the solution was concentrated under reduced pressure. After the residue obtained was washed with n-butanol, it was further concentrated under reduced pressure. A mixture of isopropanol: ethyl acetate (1:2) was added to the residue, and after insoluble materials were removed, the solution was concentrated under reduced pressure to give 2.52g of crystals (purity: almost 100%) of bicyclomycin.

Recovery: 75%.

What we claim is:

1. A process for the purification of bicyclomycin comprising adsorbing bicyclomycin with a macroporous nonionic styrene polymer adsorption resin crosslinked with divinylbenzene from an aqueous contaminated solution at a pH of about 2–8, and eluting said adsorbed bicyclomycin from said resin with a hydrophilic solvent.

2. A process according to claim 1, wherein said aqueous solution is a filtrate of culture broth containing bicyclomycin.

3. A process according to claim 1, wherein said aqueous solution contains crude solid material containing bicyclomycin.

4. A process according to claim 1, wherein said hydrophilic solvent is a lower dialkyl ketone, a lower alkanol, a mixture of said ketone and said alkanol, or an aqueous solution of said ketone, alkanol or mixture thereof.

5. A process according to claim 4, wherein said alkanol is methanol, ethanol, or propanol.

6. A process according to claim 4, wherein said dialkylketone is acetone.

* * * * *